United States Patent [19]

Scharf

[11] Patent Number: 4,991,759
[45] Date of Patent: Feb. 12, 1991

[54] DENTAL DISPENSER FOR LIGHT CURABLE SUBSTANCES

[76] Inventor: Jonathan Scharf, 364-A7 St. Andrews Rd., Glenmoore, Pa. 19343

[21] Appl. No.: 499,239

[22] Filed: Mar. 26, 1990

[51] Int. Cl.⁵ ............................................. A61C 19/02
[52] U.S. Cl. ................... 224/217; 224/218; 224/245; 206/63.5; 206/368; 206/815; 206/828; 433/163
[58] Field of Search ............... 224/217, 218, 219, 236, 224/241, 242, 245, 267; 206/1.8, 5.1, 63.5, 368, 369, 538, 539, 570, 572, 581, 815, 832, 828; 433/163, 229; 132/315; 221/185; 294/1.3, 25; 150/150, 151, 152, 153

[56] References Cited

U.S. PATENT DOCUMENTS

| | | | |
|---|---|---|---|
| 229,543 | 7/1880 | Maynard | 206/539 |
| 574,655 | 1/1897 | Beeman | 221/185 |
| 1,562,641 | 11/1925 | Hodgson | 150/153 X |
| 2,473,532 | 6/1949 | Lazare | 206/1.8 X |
| 2,869,603 | 1/1959 | Conley | 150/150 |
| 2,970,379 | 2/1961 | Hardgrove | 433/163 |
| 3,651,983 | 3/1972 | Haugen | 206/815 X |
| 4,463,879 | 8/1984 | Des Voignes | 224/217 X |
| 4,475,654 | 10/1984 | Fruchter | 206/538 |
| 4,485,925 | 12/1984 | Fickert | 206/538 X |
| 4,747,633 | 5/1988 | Stacy | 294/25 X |
| 4,822,280 | 4/1989 | Rider | 433/229 |
| 4,828,117 | 5/1989 | Panzera et al. | 206/63.5 |
| 4,844,308 | 7/1989 | Porteous | 224/217 |
| 4,913,282 | 4/1990 | Didier | 206/581 X |

FOREIGN PATENT DOCUMENTS

2085408 4/1982 United Kingdom ............... 206/828

Primary Examiner—Henry J. Recla
Assistant Examiner—Robert M. Fetsuga
Attorney, Agent, or Firm—Michael F. Petock

[57] ABSTRACT

A dispenser for maintaining light sensitive substances utilized in the practice of dentistry shielded from light and providing easy and convenient access by the dentist includes a container and a cover therefor with the cover being hingably attached to the container. The container includes a plurality of recesses for receiving one or more light sensitive substances. The container is provided with structure such as a finger hold on the bottom or an elastic band for maintaining the container on one or more digits of a hand and the cover is provided with a ring or other suitable structure for maintaining the cover in operable engagement with another digit of the hand, such as a thumb, whereby the dispenser may be held in one hand and readily opened and closed to provide easy, quick, convenient access to the light sensitive substances by the dentist.

18 Claims, 3 Drawing Sheets

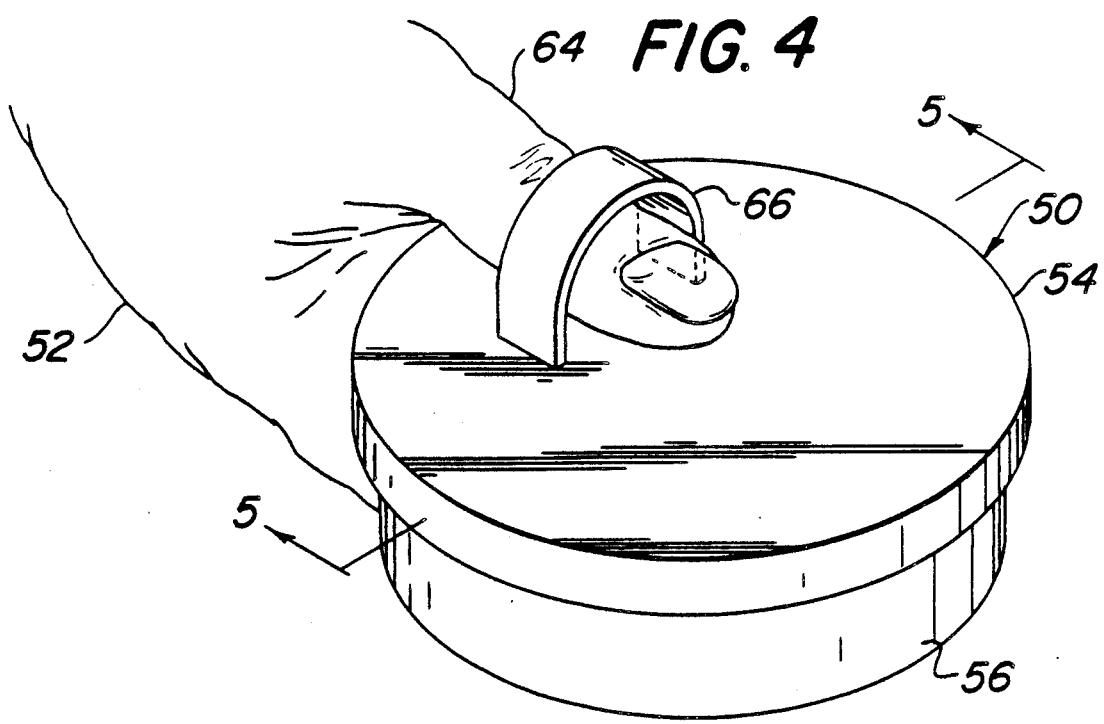
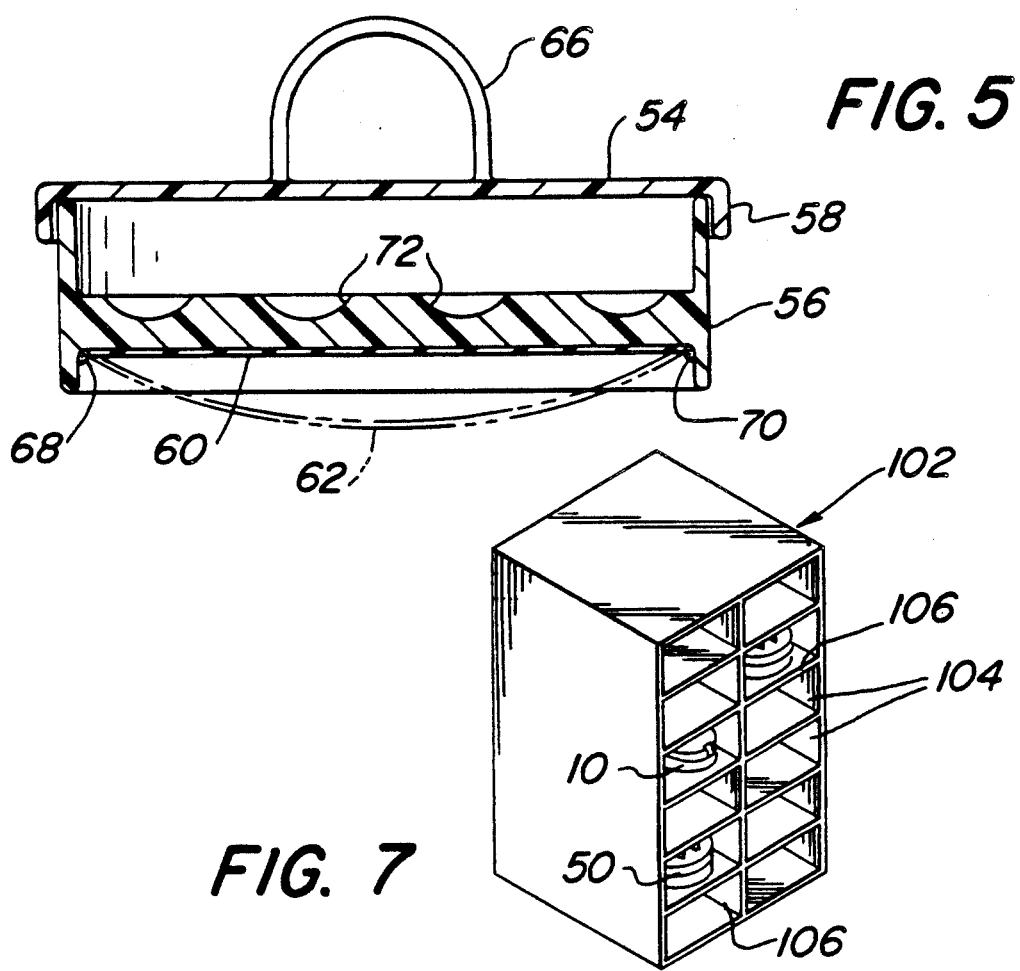

DENTAL DISPENSER FOR LIGHT CURABLE SUBSTANCES

BACKGROUND OF THE INVENTION

This invention is directed to a dental dispenser for light curable substances. More particularly, the invention relates to a dispenser which will shield light curable resins and the like from light and enable convenient use of the same as needed.

Light curable resins and the like have become widely utilized in the practice of dentistry. It is necessary that these substances be made available to the dentist as needed in performing the dental operation and shielded from light as much as possible. The light sensitive substances should be shielded from light not only during extended periods, but even during the multiple periods of time between when the dentist actually needs access to the light curable resin or the like during the dental operation.

U.S. Pat. No. 4,822,280-Rider discloses a dispenser for light curable substances wherein a box like dispenser is provided with a slidable lid for closing off the dispenser to isolate the light curable substance contained therein. This patent further discloses that the dispenser is provided with a syringe inserted into the side for the injection of the light curable substance into the container.

SUMMARY OF THE INVENTION

In accordance with the present invention, a dental dispenser for light curable substances is provided which will not only shield the light curable substances from light, but which may be easily and efficiently held and operated by a single hand. In most modern dental offices today, the dentist usually employs a dental assistant for the purpose of aiding in the dental operation in the form o handing the dentist various instruments and materials as needed as well as suctioning and providing general assistance. Accordingly, typically the dental dispenser of the present invention will be utilized by the dental assistant, and will generally be described herein in that context, although it is understood that a dentist may utilize the present invention in one hand or that it may be used by any other person in a similar manner.

One of the advantages of the present invention is that it enables effective and convenient access by the dentist to the light curable substances, such as composite resins, while maintaining the light sensitive or curable substances shielded from light.

A further advantage of the present invention is that the light shielded light sensitive substances require only one hand of the dental assistant or other person, thereby enabling the other hand of the dental assistant to be utilized for various other purposes such as suctioning or the handing of instruments or other materials to the dentist.

In accordance with the present invention, the dental dispenser is in the form of a container which may be held in one hand and opened and closed by the digits or fingers and thumb of the one hand. More specifically, the dental dispenser of the present invention is in the form of a container having a cover. The cover is preferably, but not necessarily, attached to the container at at least one point. The cover sealably mates with the container to prevent the entry of light when the cover is in sealable engagement with the container. The container includes means for receiving one or more light sensitive substances useful in the practice of dentistry. The container is provided with means for retaining the container on one or more digits of a hand and the cover is provided with means for retaining other digits of the same hand in operative engagement with the cover whereby the dispenser may be held in one hand and closed by moving the digits of one hand together and opened by moving the digits of the hand apart.

The term digit as used herein is to be interpreted to include all five fingers, i.e. or sometimes referred to as the four fingers and the thumb.

The present invention also contemplates a storage container or cabinet for storing a large number of dental dispensers wherein light curable substances, such as composite resins having, for example, pigmentation to match a number of different patients, may be stored until ready for use, such as overnight or later in the day.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 4 is a view in perspective of another embodiment of the present invention shown in the closed condition.

FIG. 5 is a cross sectional view taken along line 5—5 of FIG. 4.

FIG. 7 is a view in perspective of a storage container for the dental dispensers shown in FIGS. 1 through 6 or the equivalent thereof.

DETAILED DESCRIPTION OF THE PREFERRED EMBODIMENTS

Figure 1:
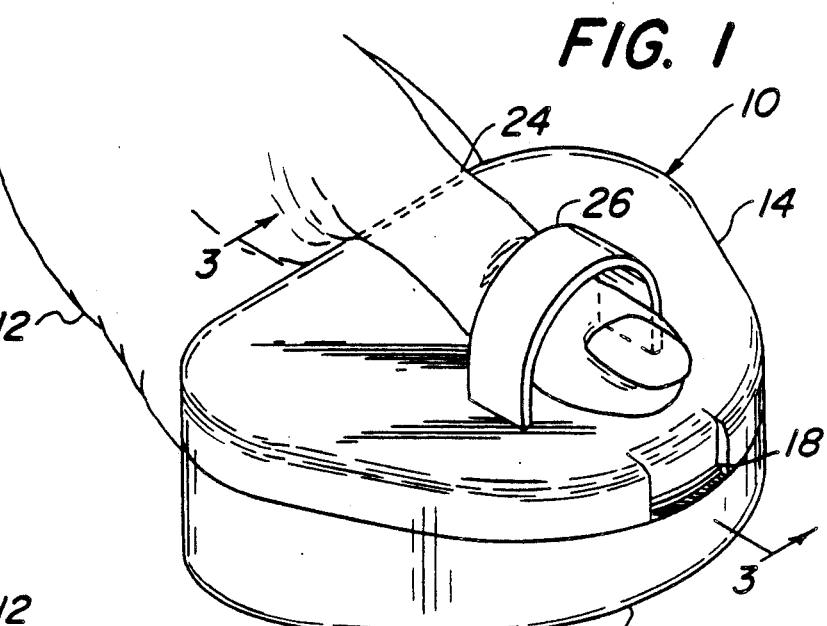
FIG. 1 is a view in perspective of a preferred embodiment of the present invention, with the dental dispenser being shown in the closed condition.
Figure 2:
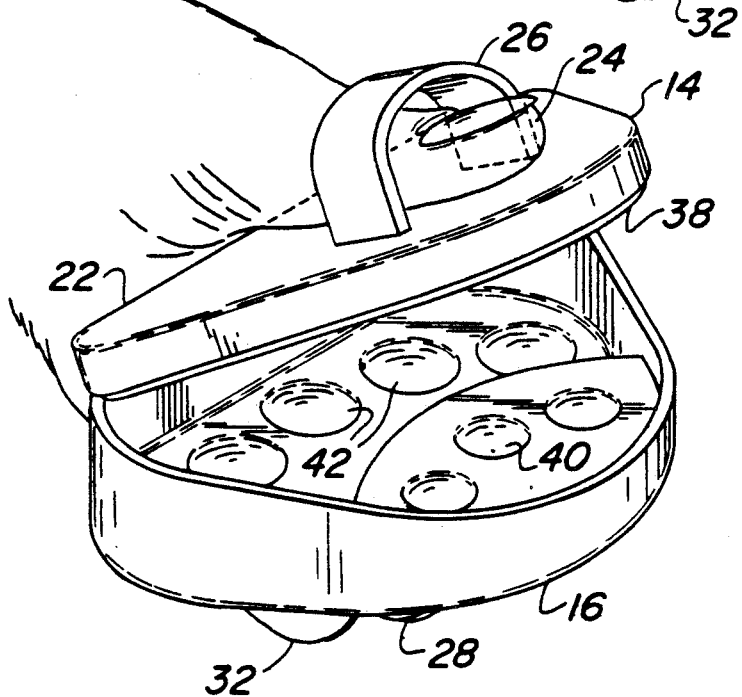
FIG. 2 is a view in perspective of a slight variation of the embodiment of the present invention shown in FIG. 1, in the open position, wherein the latching function is incorporated into the friction fit light seal between the cover and the container.

Referring now to the drawings in detail, wherein like numerals indicate like elements, there is shown in FIG. 1 a dental dispenser 10 held in one hand of a person 12, which in many cases in practical use would be a dental assistant. The fingers and the thumb of the person herein may be referred to interchangeably as digits, that is either the five digits of the hand, or as a thumb and fingers. As shown in FIGS. 1, 2 and 4, it is presently preferred that the cover of the dental dispenser might be controllably operated by the thumb and that the other fingers of the hand would be utilized to hold and control the lower container portion. However, it is understood that this could be reversed without in any way effecting the teachings herein or the scope of the present invention. For example, one of the fingers such as the forefinger or middle finger could be inserted through loop 26 or 66 instead of the thumb, and the thumb could be utilized to control the lower container portion.

Continuing to refer to FIG. 1, there is shown a cover 14 and a container 16. Cover 14 is provided with a latch 18 which is formed as an indentation in cover 10 and mates with container 16. The provision of this separate latching means 18 is the only difference between FIGS. 1 and 2, and is optional as will be described in greater detail with respect to FIG. 2. Accordingly, for ease and convenience of illustration, the same numerals will be utilized to identify the cover, container and other components in FIG. 1 through 3, and FIGS. 1 through 3 will hereinafter be described simultaneously as certain of the structure is shown more clearly in one or the other of the figures.

Figure 3:
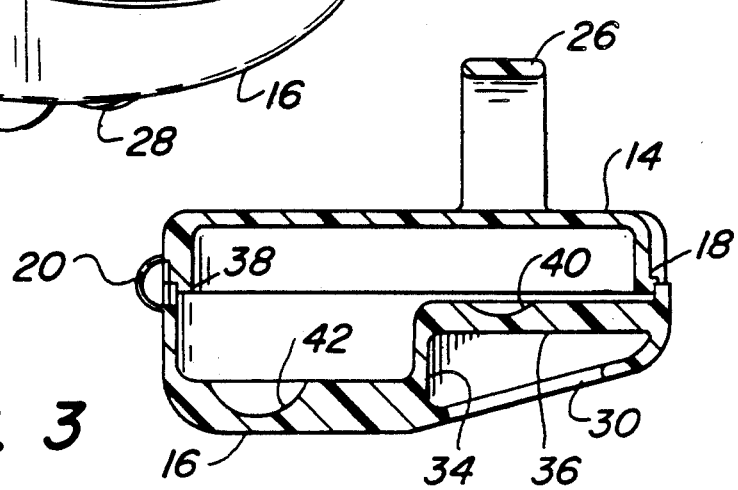
FIG. 3 is a cross sectional view taken along line 3—3 of FIG. 1.

As may be seen most clearly in FIG. 3, cover 14 is attached to container 16 by means of hinge 20. As illustrated in FIG. 3, the hinge 20 may be a flexible member attached to cover 14 and container 16, and the entire dispenser including cover 14, hinge 20 and container 16 may be molded as a unit from various well known synthetic plastic material by well known molding technology. Preferably, hinge 20 may run for a substantial length along the back surface or edge 22 of cover 14 and container 16. This back surface or edge 22 may be considered to be a diameter of a semicircle wherein the shape of cover 14 and container 16 shown in FIGS. 1–3 may be considered to be generally in the shape of a semicircle. Alternatively, hinge 20 may be of a much shorter length, referred to as a point connection or alternatively, cover 14 and container 16 may be molded separately and attached together by means of a separate mechanical hinge which may be adhesively bonded to cover 14 and container 16 or bonded by any other suitable means including sonic welding.

Figure 6:
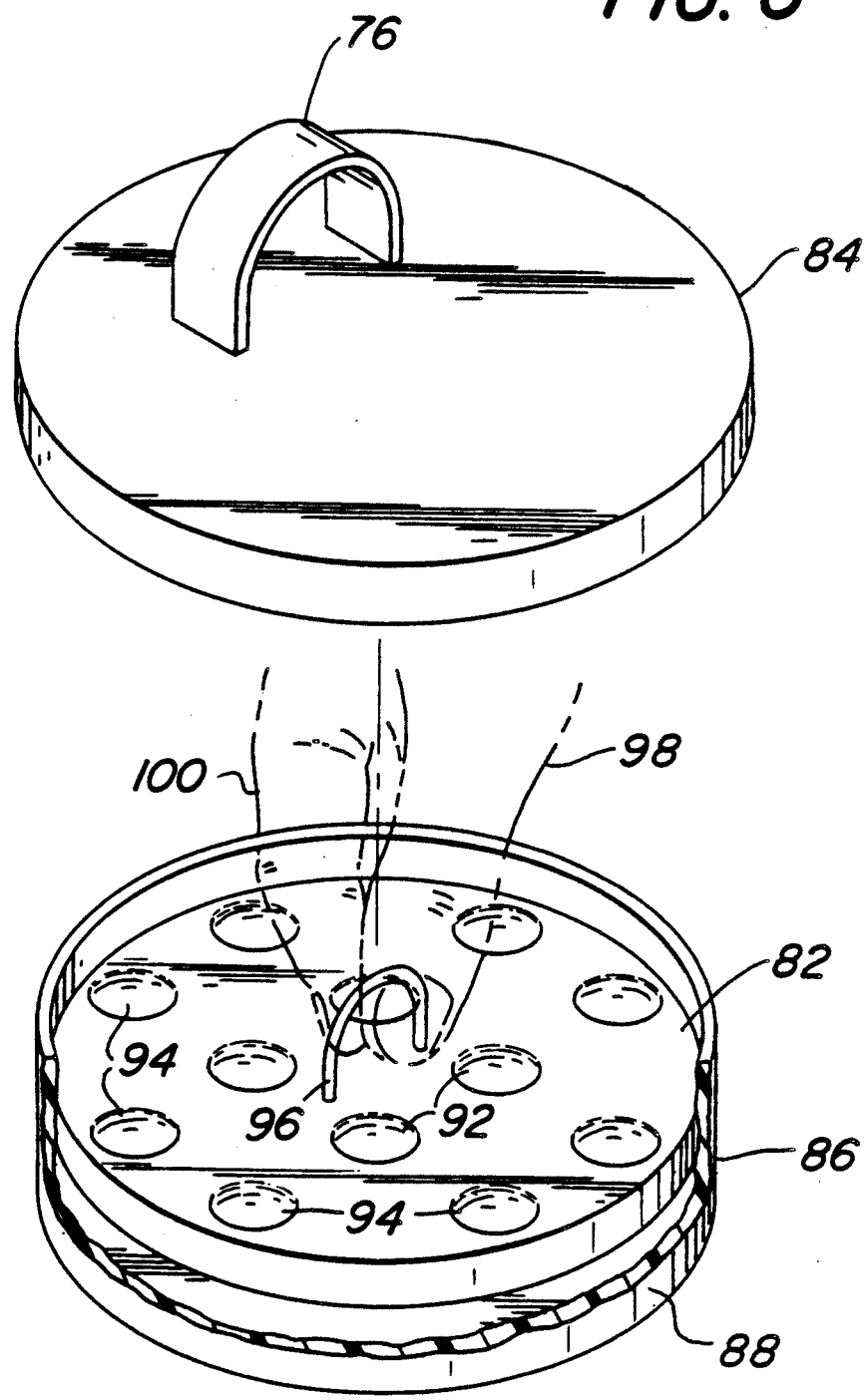
FIG. 6 is a view in perspective, partially broken away, of another embodiment of the present invention, similar to that shown in FIGS. 4 and 5, but with a removable plate containing the substance recesses, shown in the open position.

It is understood that cover 14 and container 16 for the embodiments shown in FIGS. 1 through 3 as well as the embodiments shown in FIGS. 4 through 6 and the cabinet shown in FIG. 7 may be constructed of any suitable fairly rigid material including various metals, well known synthetic plastics, paper, wood or the like. However, in certain cases where other materials are utilized, the wells or recesses for the light sensitive dental substances, such as composite resins, may have to be lined with a suitable material, such as Teflon ™ or nonreactive plastic synthetics to prevent reaction between the light sensitive dental substances and the container or its recesses. In applications where the dental dispenser of the present invention is reusable, the material utilized in constructing the dispenser should have the properties of being easily cleanable and repeatedly sterilized without adverse affect.

As shown in FIGS. 1 and 2, the dental dispenser may be held in a single hand and is preferably held between the thumb and fingers of the hand, with thumb 24 being inserted through a retaining loop 26 on cover 14 and one of the fingers 28 inserted into an opening 30 formed in the bottom of container 16. Opening 30 is provided so that one of the fingers may be hooked within the opening to firmly control and retain container 16, particularly in connection with one or more other fingers 32 positioned along the bottom surface of container 16. Opening 30 is not an opening into the container, and the inside of the container is sealed from this opening by wall portions 34 and 36 of container 16.

As may be clearly seen in FIGS. 2 and 3, a sealing lip 38 is provided on the lower surface of cover 14 which inserts into the upper portion of container 16 thereby causing cover 14 to sealably mate with the container to prevent the entry of light when the cover is in sealable engagement with container 16. As stated previously, latch 18, as a separate structure, is not required as the friction fit of lip 38 within the upper rim of container 16 effectively functions as a latch in addition to functioning as a light seal.

As may be best seen in FIGS. 2 and 3, container 16 is provided with a plurality of recesses or wells 40 and 42 for receiving the light curable substances utilized in the practice of dentistry which are typically light curable composite resins. It is desirable to have a plurality of wells arranged in a convenient manner, as a plurality of different composite resins may be required in a single dental operation and often a plurality of composite resins of substantially similar composition, but with different tints, are required for the matching of the restorative work on the teeth to the tint, color, hue, opacities, calcifications and the like of the particular patient's teeth.

Referring now to FIGS. 4 and 5, there is shown another embodiment of the present invention, including a dental dispenser 50 having a cover 54 and a container 56 held in the hand of a person 52. The dental dispenser 50 shown in FIGS. 4 and 5, as well as the dental dispenser shown in FIG. 6, include covers and containers which are provided generally with a circular or cylindrical shape. However, it is understood that various other suitable shapes may be utilized including square, rectangular, triangular and irregular shapes, as long as the cover sealably mates with the container to provide an effective light seal when the cover is closed or engaged with the container. These variations, within the scope of the present invention, are intended to include the possible variation where the openable cover could be formed of a shape which covers less then the entire shape of the container, as long as the container has a flap or structure which extends over a portion of the top of the container to form the required light seal.

As shown in FIG. 4, cover 54 is provided with a retaining loop 66, which may preferably be in the form of a semicircle, through which thumb 64 may be inserted to controllably open and close dental dispenser 50. The bottom of container 56 is provided with an elastic member, band or strap 60 attached at two spaced apart points 68 and 70 wherein one or more digits of a hand, such as fingers, may be inserted between the bottom of container 56 and elastic member 60 to retain the digits or fingers in operative engagement with container 56. Elastic member 60 is shown in dotted lines 62 in a stretched condition, wherein the fingers could be so inserted between the elastic member and the bottom of container 56.

Cover 54 is provided with a circumferential flange or lip 58 to form an effective light seal between cover 54 and container 56. The inside bottom of container 56 is provided with a plurality of recesses or wells 72 for receiving light curable dental substances useful in the practice of dentistry.

Referring now to FIG. 6, another embodiment of the present invention is shown which is similar to the embodiment disclosed in FIGS. 4 and 5 with the addition of a removable plate 82 which contains resin wells. As shown in FIG. 6, the dental dispenser includes a cover 84 and a container 86. Cover 84 is provided with a retaining loop 76. Cover 84 and retaining loop 76 are similar to that disclosed in FIGS. 4 and 5, operated in substantially the same manner and need not be described here in detail. Container 86 is similar to container 56, as shown in FIG. 5, but the bottom 88, shown broken away in FIG. 6, need not be as thick, as it does not contain any resin wells.

The outside bottom of container 86 is provided with a retaining means enabling container 86 to be retained on the hand of a person, and this retaining means could take the form of that shown and disclosed with respect to FIG. 5, a double bottom with an opening therein as shown and described with respect to FIGS. 1 through 3, or other suitable retaining means including the formation of a retaining loop similar to 26, 66 and 76 which is shown and disclosed with respect to the covers. Alternatively, although the retaining means for the container shown in FIGS. 4 and 5 is described as being preferably of an elastic member, it is understood that a non-elastic member or strap could be utilized without any significant difficulty.

With respect to removable plate 82 of FIG. 6, removable plate 82 is provided with a plurality of resin wells, which may preferably be formed and arranged in a pattern of resin wells of two concentric circles, which as shown in FIG. 6 could be comprised of an inner circle of four resin wells 82 and an outer circle of eight resin wells 94. This arrangement provides twelve wells in a particularly convenient format for use by the dentist. As shown in FIG. 6, removable resin well plate 82 may be provided with a handle 96 which may take the form of a loop as shown or any other suitable handle means which would be an aid in removing and inserting resin plate 82 from and into container 86, respectively. As illustrated in FIG. 6, handle 96 may be grasped between thumb 98 and forefinger 100 enabling insertion and removal with ease.

Referring now to FIG. 7, there is shown a storage container or cabinet 102 which may preferably be provided with a plurality of compartments 104, each of which is adapted to receive one of the dental dispensers described previously such as dental dispenser 10 or 50. Storage container 102 may be provided in the dental office wherein composite resins and other dental substances necessary for use in connection with the operation on the teeth of a particular patient may be prepared, stored in a dental dispenser and the dental dispenser then stored in one of the compartments 104 of storage container or cabinet 102. Suitable marking may be made on partitions 106 to identify the location of the dental dispenser for a particular patient.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. Apparatus for use in the practice of dentistry, comprising:
   a container and a cover both formed of a light opaque material, said cover sealably mating with said container to prevent the entry of light when said cover is in sealable engagement with said container;
   said container including therein a plurality of open recesses for receiving one or more light sensitive substances useful in the practice of dentistry;
   said cover being provided with means for retaining said cover on one or more digits of a users hand;
   said container being provided with means for retaining other digit or digits of the same hand in operative engagement with said container;
   whereby said apparatus may be retained on and opened and closed by the digits of one hand.

2. Apparatus in accordance with claim 1 wherein said light opaque container and cover are comprised of synthetic plastic material.

3. Apparatus in accordance with claim 1 wherein said container and said cover are separate members connected together at at least one point by a hinge.

4. Apparatus in accordance with claim 3 wherein said container and said cover are provided with means for latching said cover to said container, said latch means being positioned substantially opposite said hinge.

5. Apparatus in accordance with claim 1 wherein said container and said cover are comprised of a unitary member connected together at at least one point wherein said point of connection is flexible and forms a hinge-like connection.

6. Apparatus in accordance with claim 4 wherein said flexible connection is comprised of a series of points along a straight line to form a hinge like connection.

7. Apparatus in accordance with claim 1 wherein said light sensitive substances are composite resins utilized in the practice of dentistry.

8. Apparatus in accordance with claim 1 wherein said retaining means of said container is comprised of an opening formed in the lower surface of said container for the insertion of at least one digit, said opening being sealed from the inner surface of said container to prevent the entry of light.

9. Apparatus in accordance with claim 1 wherein said retaining means of said container is comprised of an elastic member mounted at spaced apart points on the outer surface of said container wherein one or more digits of the hand may be inserted between said container and said elastic member to retain said container on the digits of the hand.

10. Apparatus in accordance with claim 1 wherein said retaining means of said cover is in the form of a loop formed on the upper surface of said cover through which one or more digits of the hand may be inserted to retain it in operative engagement with said cover.

11. Apparatus in accordance with claim 10 wherein said loop is in the form of a ring.

12. Apparatus in accordance with claim 1 wherein said means for receiving one or more light sensitive substances is comprised of a removable plate member provided with said recesses for receiving substances useful in the practice of dentistry.

13. Apparatus in accordance with claim 12 wherein said removable plate member is provided with a handle for aiding in the insertion and removal of said plate member into or out of said container, respectively.

14. Apparatus in accordance with claim 12 wherein said plate is provided with two concentric circles of recesses, including a smaller circle of four recesses and a larger circle of eight recesses.

15. Apparatus in accordance with claim 1 wherein said container and cover are provided with the general shape of a semicircle having hinge means formed along at least a portion of the diameter of the semicircle.

16. Apparatus in accordance with claim 1 wherein said container and cover are provided with the general shape of a circle.

17. Apparatus in accordance with claim 1 wherein said retaining means of said container is in the form of an elastic member attached to said cover at two spaced apart points wherein one or more digits of a hand may be inserted between the container and said elastic member to retain said digits in operative engagement with said container.

18. Apparatus for storing a plurality of apparatus as set forth in claim 1 including therein a plurality of compartments, one for each apparatus.

* * * * *